(12) United States Patent
Mecklenburg et al.

(10) Patent No.: US 7,662,560 B2
(45) Date of Patent: Feb. 16, 2010

(54) BROAD SPECIFICITY AFFINITY ARRAYS: A QUALITATIVE APPROACH TO COMPLEX SAMPLE DISCRIMINATION

(75) Inventors: Michael Mecklenburg, Lavendelvagen 3, Lund (SE) 22738; Bengt Danielsson, Hiarup (SE); Fredrick Wingvist, Linkoping (SE)

(73) Assignee: Michael Mecklenburg, Lund (SE)

( * ) Notice: Subject to any disclaimer, the term of this patent is extended or adjusted under 35 U.S.C. 154(b) by 263 days.

(21) Appl. No.: 11/042,984

(22) Filed: Jan. 25, 2005

(65) Prior Publication Data

US 2005/0164274 A1 Jul. 28, 2005

Related U.S. Application Data

(60) Division of application No. 09/220,822, filed on Dec. 24, 1998, now Pat. No. 6,872,522, which is a continuation of application No. PCT/EP97/03317, filed on Jun. 24, 1997.

(30) Foreign Application Priority Data

Jun. 25, 1996 (SE) .................................... 9602545

(51) Int. Cl.
*G01N 33/533* (2006.01)
(52) U.S. Cl. ....................... 435/6; 435/7.1; 435/7.92; 435/7.94; 435/7.95; 435/960; 435/969; 435/973; 436/514; 436/518; 436/809; 422/82.01
(58) Field of Classification Search .............. 422/82.11; 436/514, 518; 435/7.1
See application file for complete search history.

(56) References Cited

U.S. PATENT DOCUMENTS 4,071,409 A    1/1978    Messing et al.
4,298,689 A *  11/1981   Doyle et al. ............... 435/7.36
4,562,157 A    12/1985   Lowe et al.
4,690,715 A    9/1987    Allara et al.
4,844,613 A *  7/1989    Batchelder et al. .......... 356/318
4,908,112 A    3/1990    Pace
4,973,493 A    11/1990   Guire (Continued)

FOREIGN PATENT DOCUMENTS

CA       2031246      6/1991
CA       2108705      5/1994
CA       2133772      5/1995
WO   WO 92/19975     11/1992
WO   WO 93/21528     10/1993

(Continued)

OTHER PUBLICATIONS

Strongin, Wendy. Laboratory Diagnosis of Viral Infections, Lennette, E. Ed. Marcel Dekker, Inc. New York. pp. 211-219.*

(Continued)

*Primary Examiner*—Bao-Thuy L Nguyen
(74) *Attorney, Agent, or Firm*—Ropes & Gray LLP; James F. Haley, Jr.

(57) ABSTRACT

Described is a method for discriminating complex biological samples using an array of discrete biological sensing elements immobilized onto a solid support in which constituents bound to the sensor array is directly determined by measuring the mass increase on the surface; data analysis of said method is performed using neutral network or statical based pattern recognition techniques. In a preferred embodiment the liquid sample is tested for the presence of soluble constituent(s) by contacting said sample with said sensor array under specific conditions, removing unbound sample constituent(s), determining the mass increase on the surface and comparising said mass increase data with a reference standard using pattern recognition software.

11 Claims, 5 Drawing Sheets

U.S. PATENT DOCUMENTS

| | | | |
|---|---|---|---|
| 4,987,032 | A | 1/1991 | Miyasaka et al. |
| 5,079,600 | A | 1/1992 | Schnur et al. |
| 5,096,807 | A | 3/1992 | Leaback |
| 5,154,808 | A | 10/1992 | Miyasaka et al. |
| 5,160,597 | A | 11/1992 | Colapicchioni et al. |
| 5,242,828 | A | 9/1993 | Bergström et al. |
| 5,252,743 | A | 10/1993 | Barrett et al. |
| 5,294,369 | A | 3/1994 | Shigekawa et al. |
| 5,342,692 | A | 8/1994 | Ribi |
| 5,384,261 | A | 1/1995 | Winkler et al. |
| 5,405,766 | A | 4/1995 | Kallury et al. |
| 5,405,783 | A | 4/1995 | Pirrung et al. |
| 5,412,087 | A | 5/1995 | McGall et al. |
| 5,429,708 | A | 7/1995 | Linford et al. |
| 5,445,934 | A | 8/1995 | Fodor et al. |
| 5,472,881 | A | 12/1995 | Beebe et al. |
| 5,512,131 | A | 4/1996 | Kumar et al. |
| 5,512,492 | A | 4/1996 | Herron et al. |
| 5,514,501 | A | 5/1996 | Tarlov |
| 5,520,787 | A | 5/1996 | Hanagan et al. |
| 5,571,410 | A | 11/1996 | Swedberg et al. |
| 5,593,838 | A | 1/1997 | Zanzucchi et al. |
| 5,603,351 | A | 2/1997 | Cherukuri et al. |
| 5,605,662 | A | 2/1997 | Heller et al. |
| 5,620,850 | A | 4/1997 | Bambad et al. |
| 5,622,826 | A | 4/1997 | Varma |
| 5,624,711 | A | 4/1997 | Sundberg et al. |
| 5,629,213 | A | 5/1997 | Kornguth et al. |
| 5,635,358 | A | 6/1997 | Wilding et al. |
| 5,653,939 | A * | 8/1997 | Hollis et al. .................. 506/3 |
| 5,677,195 | A | 10/1997 | Winkler et al. |
| 5,677,196 | A | 10/1997 | Herron et al. |
| 5,681,484 | A | 10/1997 | Zanzucchi et al. |
| 5,688,642 | A | 11/1997 | Chrisey et al. |
| 5,700,642 | A | 12/1997 | Monforte et al. |
| 5,719,060 | A | 2/1998 | Hutchens et al. |
| 5,731,152 | A | 3/1998 | Maracas et al. |
| 5,744,305 | A | 4/1998 | Fodor et al. |
| 5,810,985 | A * | 9/1998 | Bao et al. .................. 204/451 |
| 5,821,343 | A | 10/1998 | Keogh |
| 5,837,832 | A | 11/1998 | Chee et al. |
| 5,861,242 | A | 1/1999 | Chee et al. |
| 5,866,345 | A | 2/1999 | Wilding et al. |
| 5,928,880 | A | 7/1999 | Wilding et al. |
| 5,976,466 | A | 11/1999 | Ratner et al. |
| 6,228,575 | B1 | 5/2001 | Gingeras et al. |
| 6,309,822 | B1 | 10/2001 | Fodor et al. |
| 6,551,784 | B2 | 4/2003 | Fodor et al. |

FOREIGN PATENT DOCUMENTS

| | | |
|---|---|---|
| WO | WO 95/07462 | 3/1995 |
| WO | WO 95/15175 | 6/1995 |
| WO | WO 95/26634 | 10/1995 |
| WO | WO 95/28962 | 11/1995 |
| WO | WO 95/29692 | 11/1995 |
| WO | WO 96/02830 | 2/1996 |
| WO | WO 96/10178 | 4/1996 |
| WO | WO 96/26432 | 8/1996 |
| WO | WO 96/29629 | 9/1996 |
| WO | WO 96/38726 | 12/1996 |
| WO | WO 96/39937 | 12/1996 |
| WO | WO 97/07429 | 2/1997 |
| WO | WO 97/21094 | 6/1997 |

OTHER PUBLICATIONS

Carson, G. A. et al., "Self-assembly of Octadecyltrichlorosilane Monolayers on Mica," J. Materials Research, 5, (8), 1745-51 (1990).
Collioud, A. et al., "Oriented and Covalent Immobilization of Target Molecules to Solid Supports: Synthesis and Application of a Light-Activatable and Thiol-Reactive Cross-Linking Reagent," Bioconjugate Chem., 4, 528-536 (1993).
Dawson, S. L. et al., "Peptide-Derived Self-Assembled Monolayers: Adsorption of N-Stearoyl L-Cysteine Methyl Ester on Gold," Journal of Molecular Recognition, 10, 18-25 (1997).
Drickamer, K. et al., "Biology of Animal Lectins", Annual Review of Cell Biology, 9, 237-264 (1993).
Dubois, L.H. et al., "Molecular Ordering of Organosulfur Compounds on Au(111) and Au(100): Adsorption From Solution and in Ultrahigh Vacuum," J. Chem. Phys., 98, (1), 678-688 (1993).
Duschl, C. et al., "Surface Engineering: Optimization of Antigen Presentation in Self-Assembled Monolayers," Biophysical Journal, 70, 1985-1995 (1996).
Dzgoev, A. et al., "Microformat Imaging ELISA for Pesticide Determination," Anal. Chem, 68, 3364-3369 (1996).
Ekins, R. P. et al., "Multianalyte Microspot Immunoassay-Microanalytical "Compact Disk" of the Future," Clin. Chem., 37, 1955-1967 (1991).
Folkers, J.P. et al., "Self-assembled Monolayers of Alkanethiols on Gold: The Adsorption and Wetting Properties of Monolayers Derived from Two Components with Alkane Chains of Different Lengths," J. Adhesion Sci. Technol., 6, (12) 1397-1410 (1992).
Goochee, C.F. et al., "Environmental Effects on Protein Glycosylation", Biotechnology, 8, 421-427 (1990).
Hegner, M. et al., "Immobilizing DNA on Gold via Thiol Modification for Atomic Force Microscopy Imaging in Buffer Solutions," FEBS, 336, 452-456 (1993).
Hegner, M. et al., "Modified DNA Immobilized on Bioreactive Self-Assembled Monolayer on Gold for Dynamic Force Microscopy Imaging in Aqueous Buffer Solution," J. Vac. Sci. Technol. B, 14, 1418-1421 (1996).
Ikeda, K. et al., "Serum Lectin with Known Structure Activates Complement through the Classical Pathway", The Journal of Biological Chemistry, 262, 7451-7454 (1987).
Jennings, G. K. et al., "Underpotentially Deposited Metal Layers of Silver Provide Enhanced Stability to Self-Assembled Alkanethiol Monolayers on Gold," Langmuir, 12, 6173-6175 (1996).
Laine, R.A., "A calculation of all possible oligosaccharide isomers both branched and linear yields 1.05 X 1012 structures for a reducing hexasaccharide: the Isomer Barrier to development of single-method saccharide sequencing or synthesis systems", Glycobiology, 4, 759-767 (1994).
Lasky, L.A., "Selectins: Interpreters of Cell-Specific Cabohydrate Information During Inflammation", Science, 258, 964-969 (1992).
Linford, M. R. et al., "Alkyl Monolayers on Silicon Prepared from 1-Alkenes and Hydrogen-Terminated Silicon," J. Am. Chem. Soc., 117, 3145-3155 (1995).
Lundström, I. et al., "Artificial 'olfactory' images from a chemical sensor using a light-pulse technique", Nature, 352, 47-50 (1991).
Mrksich, M. et al., "Controlling Cell Attachment on Contoured Surfaces with Self-Assembled Monolayers of Alkanethiolates on Gold," Proc. Natl. Acad. Sci. USA, 93, 10775-10778 (1996).
Mårtensson, J. et al., "Interpretation of Spectroscopic Ellipsometry Data on Protein Layers on Gold Including Substrate-Layer Interactions", Langmuir, 11, 963-968 (1995).
Miller, D.J. et al., "Complementarity between sperm surface •-1,4-galactosyl-transferase and egg-coat ZP3 mediates sperm-egg binding", Nature, 357, 589-593 (1992).
Pale-Grosdemange, C. et al., "Formation of Self-Assembled Monolayers by Chemisorption of Derivatives of Oligo(Ethylene Glycol) of Structure HS (CH2) 11 (OCH2CH2) mOH on Gold," J. Am. Chem. Soc., 113, 12-20 (1991).
Parekh, R.B., "Effects of glycosylation on protein function", Current Opinion in Structural Biology, 1, 750-754 (1991).
Parekh, R.B. et al., "Cell-Type-Specific and Site-Specific N-Glycosylation of Type I and Type II Human Tissue Plasminogen Activator", Biochemistry, 28, 7644-7662 (1989).
Prime, K. L. et al., "Self-Assembled Organic Monolayers: Model Systems for Studying Absorption of Proteins at Surfaces," Science, 252, 1164-1167 (1991).
Rademacher, T.W. et al., "Glycobiology", Annual Review of Biochemistry, 57, 785-838 (1988).

Shurmer, H.V., "An electronic nose: a sensitive and discriminating substitute for a mammalian olfactory system", IEE Proceedings-G—Circuits, Devices and Systems, 137, 197-204 (1990).

Sigal, G. B. et al., "A Self-Assembled Monolayer for the Binding and Study of Histidine-Tagged Proteins by Surface Plasmon Resonance," Anal. Chem., 68, 490-497 (1996).

Sundberg, S. A. et al., "Spatially-Addressable Immobilization of Macromolecules on Solid Supports," J. Am. Chem. Soc., 117, 12050-12057 (1995).

Thompson, M.E., "Use of Layered Metal Phosphonates for the Design and Construction of Molecular Materials," Chem. Mater., 6, 1168-1175 (1994).

Varki, A., "Biological roles of oligosaccharides: all of the theories are correct", Glycobiology, 3, 97-130 (1993).

Wagner, P. et al., "Formation and in Situ Modification of Monolayers Chemisorbed on Ultraflat Template-Stripped Gold Surfaces," Langmuir, 11, 3867-3875 (1995).

Wagner, P. et al., "Covalent Immobilization of Native Biomolecules Onto Au(111) via N-Hydroxysuccinimide Ester Functionalized Self-Assembled Monolayers for Scanning Probe Microscopy," Biophysical Journal, 70, 2052-2066 (1996).

Wagner, P. et al., "•-Functionalized Self-Assembled Monolayers Chemisorbed on Ultraflat Au(111) Surfaces for Biological Scanning Probe Microscopy in Aqueous Buffers," J. Vac. Sci. Technol. B, 14, 1466-1471 (1996).

Winquist, F. et al., "Performance of an electronic nose for quality estimation of ground meat", Measurement Science and Technology, 4, 1493-1500 (1993).

Xiao, X. et al., "Chain Length Dependence of the Frictional Properties of Alkylsilane Molecules Self-Assembled on Mica Studied by Atomic Force Microscopy," Langmuir, 12, 235-237 (1996).

Folkers, J.P. et al., "Self-assembled Monolayers of Alkanethiols on Gold: The Adsorption and Wetting Properties of Monolayers Derived from Two Components with Alkane Chains of Different Lengths," J. Adhesion Sci. Technol., 6, (12) 1397-1410 (1992).

Lundström, I. et al., "Artificial 'olfactory' images from a chemical sensor using a light-pulse technique", Nature, 352, 47-50 (1991).

Miller, D.J. et al., "Complementarity between sperm surface β-1,4-galactosyl-transferase and egg-coat ZP3 mediates sperm-egg binding", Nature, 357, 589-593 (1992).

Wagner, P. et al., "ω-Functionalized Self-Assembled Monolayers Chemisorbed on Ultraflat Au(111) Surfaces for Biological Scanning Probe Microscopy in Aqueous Buffers," J. Vac. Sci. Technol. B, 14, 1466-1471 (1996).

* cited by examiner

BROAD SPECIFICITY AFFINITY ARRAYS: A QUALITATIVE APPROACH TO COMPLEX SAMPLE DISCRIMINATION

This application is a divisional of U.S. application Ser. No. 09/220,822, filed Dec. 24, 1998, which is a continuation of International Application PCT/EP97/03317, filed Jun. 24, 1997, which designated the United States, which in turn claims priority under 35 U.S.C. §119 to Swedish Patent Application 9602545-7, filed Jun. 25, 1996.

SUMMARY OF THE INVENTION

The invention takes advantage of the ability of neural network and statistical software to analyse complex patterns generated using arrays of discrete sensing elements with intermediate affinities and specificities (broad specificity) as a strategy for complex sample discrimination. Discrete sensing elements with appropriate affinities and specificities are chosen such that each element in the array has an acceptable signal to noise ratio. The informational content obtained from this assay strategy would be meaningless if analysed using conventional methods, i.e. positive vs negative type analysis. Accordingly, a pattern recognition based data analysis procedure is employed using, but not limited to, neural network and statistical software must be developed and/or adapted must be employed in order to be able to discriminate complex samples. Pattern recognition forms the basis for the discrimination process that takes full advantage of the increased informational content of this diagnostic strategy.

Thus, instead of quantitating the exact amount of a known compound that has bound to a specific sensing element (as is the case in conventional diagnostics), the bound material is quantitated by determining the increase in thickness or mass on the surface of the sensor. This can be accomplished using a number of nonlabel detection principles including, but not limited to, quartz crystal microbalances, optical techniques such as optoacoustics, reflectometry, ellipsometry and surface plasmon resonance (SPR). An essential aspect of the strategy is the fact that the constituents bound to the sensing elements need not be identified to perform the assay. This makes it possible to use recognition elements with complex interactions such as those found in nature. The samples are discriminated by correlating the values from the entire array using pattern recognition and compared to a reference sample. This increases the speed and reduces the time required to perform assays, thereby reducing costs, all of which are objects of this invention.

In one embodiment of the invention, arrays of lectins are used in combination with neural network analysis as a diagnostic tool to discriminate complex samples, such as serum samples. Lectins are immobilized onto discrete areas in an array onto planar gold coated surfaces using empirically developed high density immobilization protocols. This embodiment of the invention takes advantage of the ability of lectins to recognize saccharides, oligosaccharides and other as yet unknown ligands both natural and synthetic which have an affinity for lectins, free or attached to proteins (glycoproteins), lipids (glycolipids) and other biomolecules. The ubiquitous presence of carbohydrates in all living organisms provides a nearly universal means for identification of complex biological samples. The complex biosynthetic pathways used to synthesize these carbohydrates are effected by subtle changes in their environment. These changes lead to a series of complex global modifications in the composition and thereby the structure of the carbohydrates.

This invention takes advantage of this diversity in order to increase the amount of information that can be obtained, instead of quantitating the exact amount of a particular compound that has bound to a specific lectin as is routinely done in conventional diagnostics. The use of arrays of lectins enables the identification of global changes in complex samples, thereby allowing discrimination. We assume many different substances with a wide range of affinities for a particular sensing element are competing for the recognition sites on the lectins. An additional object of the invention is the ability of the assay strategy to take advantage of as yet unidentified recognition capabilities present on biomolecules. These unidentified recognition elements will provide information that allow the discrimination of samples with unprecedented accuracy and presently not possible with any other diagnostic assay strategy. This complex interplay provides a wealth of data which, due to the rapid development in computer technology and signal processing techniques, can be rapidly analysed. Moreover, the ability of sensing element arrays will grow dramatically as more biomolecules are tested in the assay and their unknown recognition functions become evident.

An application of this invention involves the use of lectin arrays to discriminate sera from different animal species. In these studies, the constituent(s) bound to each lectin in the array is quantitated using a fixed angle ellipsometer. The responses obtained from these experiments were used to train the artificial neural network. Using appropriate normalization methods, the resulting trained network was able to discriminate all of the serum samples. The assay shows the utility of the invention for the general identification of complex biological material. Another application of the lectin affinity array was for the discrimination of "healthy" and "sick" individuals (humans). These experiments show, that even subtle changes in serum composition such as those associated with mild bacterial infections can be identified (using artificial neural networks with appropriate normalization). In these experiments, the substance(s) bound to the lectins were quantitated using the SPR detection principle. This shows that sample discrimination is not dependent upon a particular nonlabel technique but is universally applicable to any detector that is capable of unloosing substances bound to the sensing elements in nonlabel modes.

BACKGROUND OF THE INVENTION

Figure 1A:
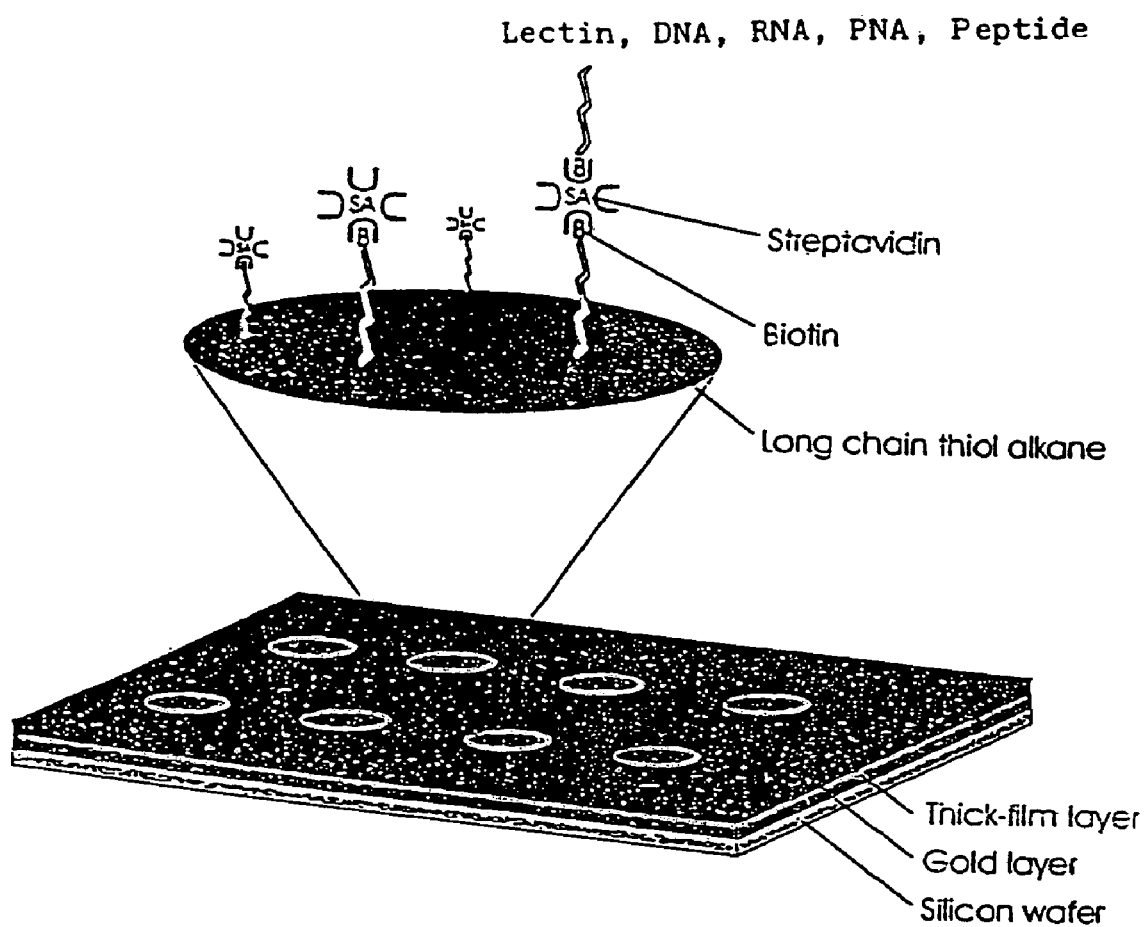
FIG. 1a. Schematic overview of the immobilization procedure using 8 sensing fields.

Chemical sensor arrays can be used to identify and classify complex gas mixtures or odors (Shurmer, H. V., An electronic nose: A sensitive and discriminating substitute for a mammalian olfactory system, IEEE proc. G 137, 197-204, 1990; Gardner, J. W. and Bartlett, P. N. (eds), Sensors and Sensory Systems for an Electronic Nose, Proc. NATO Advances Research Workshop, Reykjavik, 1992.). Chemical sensors are in general non-specific, but have different selectivity patterns towards the species in the odor. More specifically, it has been demonstrated how large sensing surfaces consisting of different catalytic metals in metal-oxide-semiconductor field effect structures can be used together with an optical evaluation technique to obtain visually identifiable images of odors (I. Lundström, R. Erlandsson, U. Frykman, E. Hedborg, A. Spetz, H. Sundgren, S. Welin, and F. Winquist, Artificial 'olfactory' images from a chemical sensor using a light-pulse technique Nature, 352, 47-50, 1991. It is important to note that this increased informational content is derived from the (continuous) varying selectivity profile along the sensing surface for the sensor array. No discrete recognition elements are known to exist. Different pattern recognition methods based on statistical approaches or artificial neural networks can be used to evaluate the signal patterns from these sensors. The devices have been used to analyze a variety of food stuffs (Winquist, F., Hörnsten, E. G., Sundgren, H. and Lundström, I., Performance of an electronic nose for quality estimation of ground meat, Meas. Sci. Technol. 4, 1493-1500, 1993.; Winquist, F., Hörnsten, G., Holmberg, M., Nilsson, L. And Lundström, I. Classification of bacteria using a simplified sensor array and neural nets", submitted).

DETAILED DESCRIPTION OF THE INVENTION

New sensor concept. The analogy between these sensors and that of biological sensing systems, such as the olfactory system, has been conceptually important in driving the development of this technology. The basis for the human olfactory sense is that a signal pattern is generated from the receptors cells in the olfactory bulb. The receptor cells are not specific for a particular molecules, but rather belong to different selectivity classes. The basis for olfaction (smell) appears to combine the signals obtained from each of the low specificity receptor classes. The combinatorial effect that results leads to an increase in the discriminatory ability of the system (despite the relatively small number of receptor classes). The chemical sensing elements can recognize odors but lack the discrete recognition capabilities that biomolecules and synthetic biomimetic molecules possess. As noted, chemical sensors use continuous gradients and other approaches as recognition elements and are not discrete. Nature uses discrete identifiable sensing elements which have evolved recognition capabilities in a biological context. One object of the invention is to apply discrete biosensing elements in a fashion that increases the informational content of the diagnostic assay. This would require the employment of a biomolecule with broad recognition characteristics which would normally be considered too ill-defined to be useful in conventional diagnostics. The specificity must be chosen so as to obtain adequately broad binding (high informational content) but not so much as to make differentiation between specific and nonspecific binding impossible, i.e. adequate signal to noise ratio. At the same time, biological sensing elements must have well defined binding characteristics that are appropriate for this assay strategy.

The invention described here involves the development of a new assay strategy for complex sample discrimination using arrays of biorecognition elements that is far more informationally rich than conventional assays. Another object of this invention is to reduce the number of tests that must be performed before a diagnosis can be made, thereby reducing the time required to start treatment as well as the cost. Unlike standard diagnostic tests which detect known compounds highly specifically, we detect the binding of unknown compounds to the lectins. Thus, the new assay strategy requires the employment of specialized nonlabel-based detection techniques, including but not limited to quartz crystal microbalances and optical techniques such as optoacoustics, reflectometry, ellipsometry and surface plasmon resonance (SPR). All of the methods that are based on polarized light reflected off a solid surface have already proven valuable for thickness determination of proteins on solid surfaces. The sensitivity of the methods are about the same, which is on the order of a few ångströms.

Biological sensing elements. Proteins have the ability to combine specifically and reversibly with a variety of ligands. Enzymes for example bind substrates and inhibitors while antibodies can be produced which bind a variety of antigens such as carbohydrates, proteins, and small molecules. Another class of proteins, lectins, have the ability to bind sugars and are devoid of enzymatic activity. Receptors bind a wide range of ligands with high affinity and specificity. Nature evolves and maintains proteins for specific purposes with adequate affinity and specificity for a particular purpose. Thus, the employment of biological or synthetic biomimetic sensing elements is the most appropriate approach for identifying changes that are of biological significance. We have chosen to test the biosensing affinity arrays invention described here using the lectins. We shall describe lectins and give several advantages this class of proteins has over the more commonly used immune-based diagnostics in the application of this invention.

Lectins as biological recognition elements. As mentioned previously, lectins bind carbohydrates and to compounds with similar structure. (Lectins as molecules and as tools. Lis, H. And Sharon, N. Ann. Rev. Biochem., 55, 35-67, 1986; Advances in Lectin Research. Vol 1, Franz, H. Ed., Springer-Verlag, Berlin, 187 pp., 1987). Lectins also have the capability to agglutinate cells, precipitating polysaccharides and glycoproteins and are of nonimmune origin. This is due to the fact that they are oligomeric in structure, usually containing one sugar binding site per subunit. In this respect, lectins have agglutinating abilities similar to those of antibodies. They also can be inhibited by low molecular weight compounds, which in the case of lectins are small carbohydrates, such as monosaccharide, oligosaccharides or macromolecules which contain them.

First, lectins provide a broad spectrum of well defined binding specificities with a high degree of cross reactivities as compared for example with antibodies and enzymes. Furthermore, they are stable and have a wide range of affinities and specificities. In addition, over one hundred lectins have been characterized. It now appears that lectins mediate a variety of cellular interactions during development and in the adult animal (Drickamer, K. And Taylor, M. E. Biology of Animal Lectins Annu. Rev. Cell Biol. 9:237-64, 1993). This is supported by data which shows that lectin expression patterns change throughout development and in response to a wide range of environmental changes [Varki, A. Biological roles of oligosaccharides: all of the theories are correct, Glycobiology, 3:97-130, 1993.]. The involvement of oligosaccharides in selectin-mediated cell-cell recognition by the immune system in response to inflammation [Lasky, L. A. Selectins: interpreters of cell-specific carbohydrate information during inflammation. Science 258:964-969, 1992 and sperm-cell recognition during fertilization [Miller, D. J., Macek, M. B., Shur, B. D. Complementarity between sperm surface b1,4-galactosyltransferase and egg coat ZP3 mediates sperm-egg binding. Nature 357:589-593, 1992) are but a few examples. It is also known that modifying the expression of glycosides and glycosyltransferases interferes with normal development. However, it has not been possible to define the individual contributions of individual monosaccharides residues and oligosaccharide chains to stage-specific and tissue-specific developmental processes.

An object of this invention is the ability of the assay strategy to discriminate complex samples which could be used to delineate complex basic developmental processes.

Second, the study of lectins is intimately linked to that of carbohydrates and is referred to as glycobiology (*Glycoproteins*, Hughes, R. C. outline Studies in Biology, Chapman and Hall, London and New York, 95 pp, 1983). Glycosylation is used extensively in nature for a wide range of purposes some general, such as protease protection, some directed to particular classes of proteins, such as signaling mechanism for clearance of proteins from serum and some highly specific, such as cell adhesion. Carbohydrates also act as control mechanisms, as signals for cellular localization, for specific cell surface recognition of one cell type by another, for clearance of a particular glycoform from serum, assist in protein folding possibly by providing protection against proteolysis (Pareth, R. B. Effects of glycosylation on protein function. Curr. Opin. Struct. Biol. 1:750-54, 1991).

Carbohydrates contain a potential informational content several orders of magnitude greater than any other biological oligomer. For example, if one calculates the number of possible structures for a hexamer of sugars and that of a hexamer of amino acids, the figure is $>1.05 \times 10^{12}$ and $4.6 \times 10^{4}$. The difference is more than seven orders of magnitude. Accordingly, sugars clearly provide the largest single source of diversity in the biological world (Laine, R. A. Invited Commentary in Glyco-Forum section Glycobiology 1994 8, 759-767).

Lectins have also been shown to be important in defence against a variety of pathogens. The mannose binding lectins in animals mediates antibody-independent binding of pathogens which contain a high concentration of mannose on their surface. These monosaccharides are not generally found in terminal positions on serum or cell surface glycoproteins in mammalian systems. The recognition event can initiate the complement cascade [Ikeda, K, Sannoh, T., Kawasaki, T. And Yamashima, I. (1987) J. Biol. Chem. 262, 7451-7454.]. Plant lectins have also been implicated in attachment of symbiotic nitrogen fixing bacteria to the roots of leguminous plants and int eh protection of plants against fungal pathogens (Bohlool, B. B. and Schmidt, E. L. (1974) Science 185:269-71).

Third, numerous pathogens use carbohydrate-lectin interactions in order to gain entry into their hosts. For example, bacteria and intestinal parasites, such as amoeba, mediate the sugar specific adherence of the organisms to epithelial cells and thus facilitate infection. (Liener, I. E., Sharon, N., Goldstein, I. J. eds (1986) The Lectins: Properties, functions and applications in biology and medicine. New York: Academic.). Viruses such as influenza virus (myxovirus) and Sendia virus (paramyxovirus) use a haemagglutonin protein that binds sialic acid containing receptors on the surface of target cells to initiate the virus-cell interaction (Paulsson, J. C. Interaction of animal viruses with cell surface receptors in: The Receptors (Vol. 2) (ed. P. M. Conn), Academic Press, New York, pp. 131-219, 1985).

Another object of the invention is to study the pathogenesis of diseases that use carbohydrates or lectins in order to gain entry into cells.

Carbohydrate binding proteins such as selectins are believed to play a critical role in immune responses including inflammation (Springer, et al. 1991 Nature 349:196-197; Philips, et al., 1990 Science 250:1130-32. Specific carbohydrate ligands have been identified and have been used to control inflammation, immunosuppression, etc. through their interaction with selectin proteins and/or other lectins (Gaeta, et al., U.S. Pat. No. 5,576,305 corresponding to U.S. patent application Ser. No. 07/538,853, filed 15 Jun. 1990; Ippolito, et al., U.S. Pat. No. 5,374,655 corresponding to U.S. patent application Ser. No. 07/889,017, filed 26 May 1992). Other glycoproteins have also been shown to be useful in suppressing mammalian immune responses (Smith et al., U.S. Pat. No. 5,453,272 corresponding to U.S. patent application Ser. No. 07/956,043 filed 2 Oct. 1992).

Another object of the invention is to use the assay strategy in order to delineating the more subtle recognition functions of lectins, including but not limited to selectin and other lectins, in immune and inflammatory responses.

Fourth, the wide distribution of and ready availability of large numbers of sugars and sugar binding proteins combined with their ubiquity throughout nature, has led to their extensive use as reagents for studying carbohydrates in solution and on cell surfaces. They were originally used for blood typing (Lis and Sharon), for the identification and separation of cells (Sharon, N. 1983 *Adv. Immunol.* 34:213-98). Labelled lectins serve as specific reagents for the detection of glycoproteins separated on gels, either directly or after blotting (Rohringer, R., Holden, D. W. 1985 *Anal. Biochem.* 144:118-27.) Immobilized lectins are routinely used for isolating glycoproteins such as the insulin receptor (Hedo; J. A., Harrison, L. C., Roth, J. 1981 Biochemistry 20:3385-93) and the many others proteins. Lectins have been widely used to separate cells such as thymocytes and splenocytes (Reisner, Y, Sharon, N. 1984 Methods Enzymol. 108:168-79; Maekawa, M., Nishimune, Y. 1985 Biol. Reprod. 32:419-25.). Numerous bacteria have been typed using lectins (Doyle, R. J., Keller, K. F. 1984 *Can. J. Microbiol.* 3:4-9; DeLucca, A. J. II 1984 *Can. J. Microbiol.* 3:1100-4). Primates can be differentiated from non-primates by the presence of specific sugar residues [Spiro, R. G. and Bhoyroo, V. D. (1984) J. Biol. Chem. 259, 9858-9866; Galili, U., Shohet, S. B., Kobrin, E. Kobrin, E., Stults, C. L. M., and Macher, B. A. (1988) J. Biol. Chem. 263, 17755-17762. These applications are strictly dependent upon the ability of a particular lectin to specifically identify a carbohydrate attached either to a soluble biomolecule or to a cell or organelle.

Fifth, most cells have a coating of carbohydrate chains in the form of membrane glycoproteins and glycolipids (in eukaryotes) or of polysaccharides (in prokaryotes). In eukaryotes, the cell type and environmental factors such as glucose concentration, play a major role in determining the extent and type of glycosylation, which is both species and tissue specific (Parekh, R. B., Dwek, R. A., Thomas, J. R., Opdenakker, G., Rademacher, T. W. (1989) Biochemistry 28, 7644-7662; Goochee, C. F. and Monica, T. (1990) Bio/Technology 8, 421-427). In addition, each individual enzymatic reaction may or may not go to completion, giving rise to glycoforms or glycosylated variants of the protein (Rademacher, et al. Ann. Rev. Biocehm., 1988 57:789-838). These factors give rise to the enormous heterogeneity of carbohydrate structures found in vivo that has hindered their analysis. However, in some instances the relative concentration of the different forms have been shown to vary in specific ways in certain health and disease states. For example This also explains why glycosylation patterns of natural glycoproteins may be influenced by physiological changes such as pregnancy and also diseases such as rheumatoid arthritis.

In addition, it is known that the interaction between individual monosaccharides and CRDs is too weak to account for the affinities that lectins have for glycoproteins. The oligomeric lectins (multivalent) clusters the carbohydrate recognition domains (CRDs) which increases both the specificity and the affinity for multibranched oligosaccharides. While these effects are not well understood, it is clear that the density of CRD has biological significance. Thus, is an additional parameter that can be used in the invention to further increase the informational content of the assay. This would indicate that lectins could be useful following changes in the overall state of complex biological samples. This wealth of diversity provides a nearly unlimited range of sensor elements from which to choose.

It is believed that the multivalency of lectins for carbohydrates is important for their biological activity. Thus, an object of the invention would be the application of density gradients of lectins on surfaces in continuos and discontinuous, as well as in homogeneous and heterogeneous formats for sample discrimination. This would provide a unique tool for gaining a basic understanding of the effect of binding site density on the recognition process. Methods are available to those skilled in the art for adapting reflectometry, ellipsometry or SPR for scanning and imaging modes. This also would provide an additional assay parameter, thus increasing the informational content of the lectin affinity arrays and thereby improving their ability to discriminate complex samples.

Diagnostic assays strategies. Immunoassay based diagnostics currently predominate the market, nevertheless, lectins provide some advantages over conventional immunoassays. Lectins are present in most life forms and more importantly they are found in life forms such as plants, microorganisms and viruses, which do not synthesize immunoglobulin. Clearly the biological function(s) of lectins precedes that of the immune system, many of which are unknown at present. Thus, these sensing elements will be more useful for identification and classification purposes. The extensive homologies observed between different classes of lectins demonstrate that these proteins have been conserved throughout evolution and provide strong evidence that they have important function(s) in biology. Another difference is that lectins are structurally diverse whereas antibodies are structurally similar. This structural diversity would result in a corresponding diversity of stabilities that would increase the flexibility of the assay formats (antibodies tends to denature under similar conditions due to their structural similarity). Thus, lectins combine the multivalency of antibodies with the structural diversity of enzymes. Other proteins which bind carbohydrates also exist such as those that participate in carbohydrate metabolism and sugar transport. In general, these proteins only bind one carbohydrate and serve quite different purposes than lectins.

The detection of specified antigens, haptens and the like substances in bodily fluids such as blood, serum, sputum, urine, and the like is of central importance in both research and clinical environments. The detection of such ligands can often be correlated to various disease states and consequently, is of great importance in diagnosis and for gaining a basic understanding concerning the genesis of disease, as well as for monitoring the efficacy of therapeutic treatments. The large and ever increasing ability to diagnose and treat diseases has lead to an explosive increase in demand for diagnostic testing. And while the cost per assay has been reduced, the number of tests that are performed has increased dramatically. This is in part due to the increasing number of tests that are available and in part due to the need medical practitioners have to be able to justify their actions in the event that legal action (malpractice suits) should be taken against them.

Accordingly, improved methods for detecting ligands in aqueous samples are constantly being sought. In particular, such preferred methods or assays are those that are faster, more flexibility, simpler to perform and manufacture, as well as having low manufacturing costs. In addition, there is an increasing need for strategies that will reduce the time necessary to develop diagnostic assays for such agents as HIV and Bovine Spongiform Encephalitis (BSE). Increasing health costs require the development of new, rapid, and more effective diagnostic strategies.

In general, immunoassays are based upon the immunological reaction between proteins such as antibodies, antibody fragments, or even artificially generated elements simulating antibody binding sites such as peptides, templated polymers and the like (hereafter referred to as antibody recognition) and the substance for which they are specific, the ligand. Immunological reactions are characterized by their high specificity and accordingly, numerous schemes have been developed in order to take advantage of this characteristic. The goal is to identify a particular state with absolute specificity using as few assays as possible.

In the traditional heterogeneous forward assay, an antibody is immobilized on a solid phase such as microparticles, microtiter wells, paddles, and the like. The sample is then contacted with the immobilized antibody and the ligand binds if present in the sample. The bound substance is detected and quantitated by an entity associated directly or indirectly therewith. Such detectable entity include fluorescent molecules, chemiluminescent molecules, enzyme, isotopes, microparticles and the like. Many variants have been developed such as competition, indirect competition, and the like. Various methods are available to those skilled in the art for quantitating the amount of substance bound using these assays.

In addition to immunoassays, other diagnostic assays are available based upon the same demand for absolute specificity using wide range of recognition elements such as proteins (lectins, receptors, and the like), nucleic acids, carbohydrates, lipids and/or synthetic/engineered biomimetic compounds and the like. A wide range of basic techniques have also been developed including but not limited to microscopy, chromatography and electrophoresis in order to specifically identify diseases.

It is an object of this invention to provide an assay strategy for sample discrimination which relies upon an array of sensing elements with low specificity in order to increase the informational content of the diagnostic assay. The assay strategy is capable of discriminating subtle changes and thus allows early identification of changes in the state of health that can be of crucial importance. In some instances, the sensing elements used in conventional assays will be applicable. However, in most instances the specificity of these reagents will be too high to allow their use. Accordingly, new screening procedures will be developed in order to isolated reagents with appropriate combination of affinities and specificities and is an object of this invention, as well.

The assay strategy can be extended to a wide range of applications that require complex sample discrimination including but not limited to identification of diseases, identification of changes caused by the disease itself in the host (including but not limited to human, animal, plants and microorganisms). Complex samples containing biological material and/or degradation products including but not limited to such as food stuffs like beverages, dry foods, and the like (including but not limited to quality control, for detection of unwanted microbial growth, freshness, physical damage), as well as the control of environmental samples for microbial flora (including but not limited to microbial content and composition), pollutants and their breakdown products in air, soil and water samples. This strategy and assays based on it could also be used for monitoring fermentation processes, including but not limited to yogurt, beer, wine and the like, broths, as well as in fermentation processes in which products are produced such as biological compounds produced by microbial processes, such as insulin from genetically engineered bacteria and the like, as well as condiments made for seasoning and the like, as well fermentation processes used in the production of animal food stuffs.

Current diagnostic testing approaches used to determine the general state of health such as hemagloblin, blood pressure and the like give only limited information. And while these tests provide useful information as to the general state of health, they do not provide adequate information to identify diseases nor are they sensitive enough to detect subtle changes required for early disease detection. There is a need, therefore, to develop new strategies for the identification of disease states which provide information as to which class of ailments the patient is suffering in order to reduce the number of specific tests which must be performed.

Another object of the invention is to provide a strategy and assays for improved techniques to monitor the general state of health to assist efforts in identifying ailments early on thereby allowing treatment to begin at an earlier stage than would have been possible otherwise. The early treatment of disease has been shown to reduce health care costs. This strategy would also be useful in preventative health care schemes. A similar situation exists in food stuff and environmental testing.

This diagnostic strategy based on the use of discrete recognition elements with broad recognition specificities combined with computer based artificial neural network data analysis can also be used with discrete synthetic biomimetic recognition elements with appropriate specificity (signal to noise). These could be made from modified biological material or from polymeric materials by conventional templating techniques and the like. This embodiment of the invention would be especially useful in applications requiring assay conditions that would destroy or dramatically reduce the binding affinity and/or specificity of conventional biological sensing elements including but not limited to organic solvents, high or low temperature, acidic or basic solutions and salts.

These detection techniques demand highly reproducible, high density immobilization methods for flat surfaces such as silicon wafers or flat glass. Other surfaces compatible with these detection techniques including but not limited to plastic, silicon, mica and glass surfaces in both metal coated or uncoated. Standard immobilization protocols resulted in poor overall reproducibility due to inadequate signal to noise ratios. A method was developed that allowed high density immobilization of biomolecules with high retention of biological activity while minimizing nonspecific binding assay. The increased sensitivity and reduced nonspecific binding achieved increased the signal to noise ratio that was essential for this assay strategy. We now believe that the nearly 100% surface coverage. This prevents interaction directly with the metal surface, and provides an essentially homogenous interaction matrix, and maximizes surface densities.

The strategy could be used to discriminate complex samples from other origins including but not limited to, body fluids such as blood, serum, saliva, sputum, urine and the like, thus allowing complex correlations with known reference standards (using pattern recognition programs). Environmental samples such as air, soil, water and the like, food stuffs and the like as well as artificial substances for which appropriate sensing elements can be found could be analysed using this strategy, i.e. appropriate signal to noise ratios can be obtained for the samples in question. No analytical approach can currently exists which can discriminate samples as rapidly or as cost effectively. An important object of the invention is the ability of the strategy to take advantage of as yet unknown recognition functions present in the recognition elements.

We have not made any attempt to identify the substances bound to the lectin arrays but various methods are available to those skilled in the art of identifying biomolecules to perform this type of analysis. While this is not the primary aim of the invention, it may prove useful for understanding the nature of changes that have occurred that may assist in the development of therapies and/or the development of therapeutic drugs. In addition, any recognition element which exhibits the characteristics required by this assay strategy, including but not limited to biomolecules such as proteins, lipids, carbohydrates and nucleic acids, modified biomolecules, such as genetically engineered, chemically modified, and the like, as well as synthetic molecules used in molecular recognition, such as cyclodextrans, templated and imprinted polymers and the like, may also be used in this regime.

Another object of the invention is the combined approach used to immobilize the biomolecules and included special surfaces (gold), hydrophobic thick-film patterning, self-assembling long chain thiols with terminal carboxylic acid groups and an empirically determined EDC/NHS immobilization protocol. While all of these have been used individually, no immobilization protocol exists which combines these various techniques into a single unified protocol.

Numerous patents have been disclosed which employ a wide range of biological sensing elements for diagnostic and therapeutic purposes, such as WO 95/29692, WO 95/15175, WO 95/28962, WO 95/07462, Canadian patent 2,133,772, U.S. Pat. No. 4,289,747, U.S. Pat. No. 4,389,392, U.S. Pat. No. 4,298,689 and WO 95/26634. All of these inventions use the unique specificity of some sensing element, be it an antibody or a lectin, to identify a single disease (or groups of highly related diseases). Great attempts are made to increase the specific reaction and reduce the nonspecific reactions, in strong contrast to the invention described here.

WO patent 92/19975 describes a method for labelling glycoproteins with a fluorescent molecule in a complex mixture using a carbohydrate specific labelling reagent. This mixture of labelled proteins is separated and the banding pattern analysed using pattern recognition techniques.

Our invention has several advantages over this invention. First, no separation steps are involved which reduces the time, labour, cost and complexity of the assay. Second, no recognition elements are used, limiting the flexibility of the assay. Third, since no recognition elements are used the analysis of known or unknown binding functions is not possible. And finally, the assay cannot be expanded which restricts the ability of the assay to take full advantage of pattern recognition programs.

Example 1

Figure 1B:
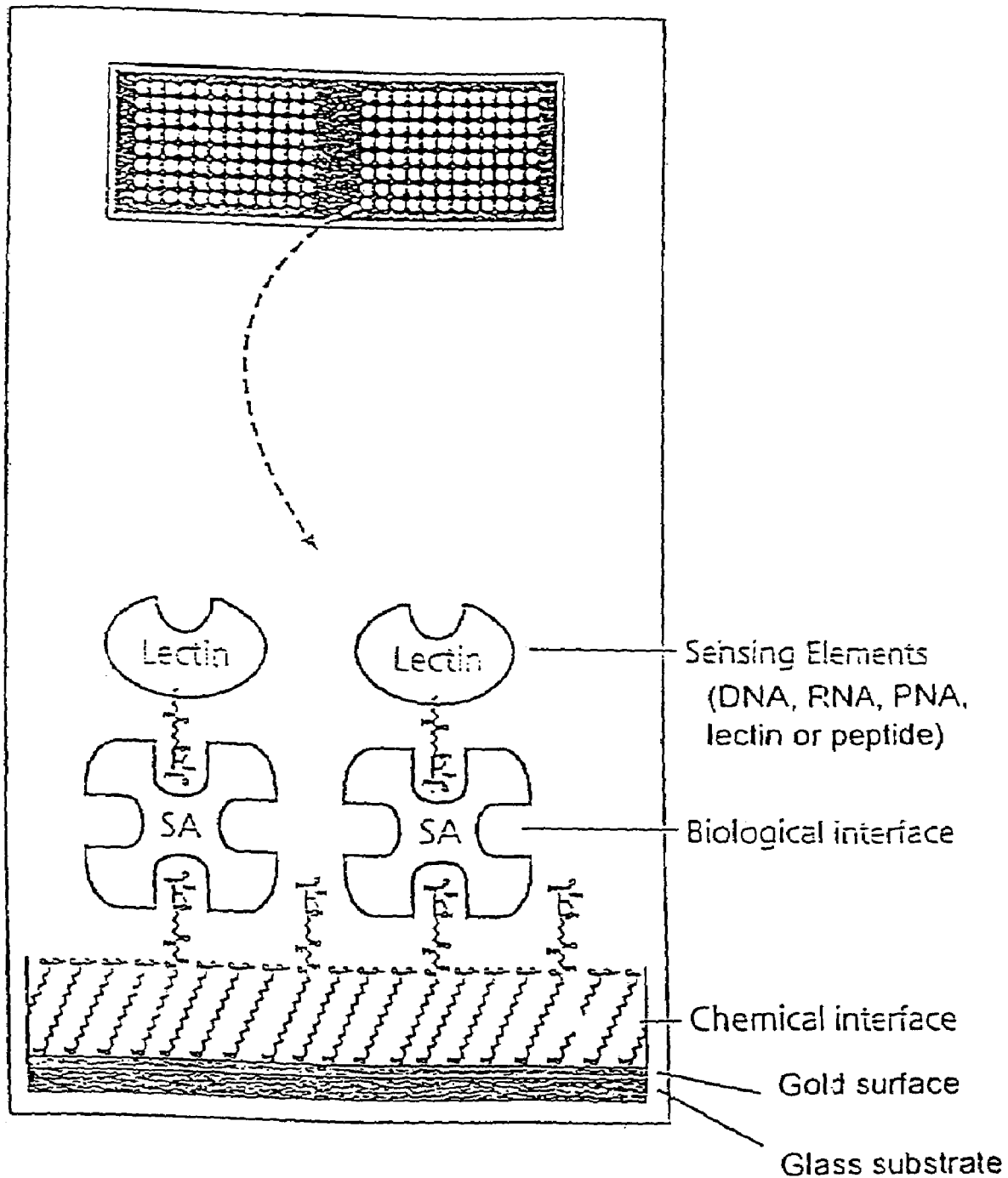
FIG. 1b. Schematic overview of the immobilization procedure using 2×96 sensing.

Interfacing these biological sensing elements with the surface mass based optical imaging technology was very difficult. Standard immobilization protocols resulted in poor overall reproducibility and lead us to develop a highly specialized protocol which combines surface patterning and immobilization technologies (FIG. 1). The integrated assay format which combines thick film surface patterning, self-assembling monolayers, efficient coupling chemistries and the biotin-streptavidin. The procedure employs a proprietary teflon based thick-film printing ink (Cell-line, USA) to pattern gold coated silicon wafers or glass combined with self-assembling carboxyl-terminated long chain thiol alkanes onto the exposed gold surfaces. Polished silicon wafers (Wacker Chemie, Germany) or glass were coated with gold by evaporation as described (Mårtensson, J., Arwin, H. Intepretation of spectroscopic ellipsometric data on protein layers on gold including substrate-layer interactions. (1995) Langmuir 11:963-968.). These surfaces were then patterned with a proprietary hydrophobic coating using thick-film technology (Cell-line, USA). The hydrophobic thick-film patterning greatly simplified localization of the various reagents which lead to a dramatic improvement in the overall reproducibility of the assay protocol. The wafers were sonicated in EtOH prior to being treated with HS—$(CH_2)_{16}$—COOH (1 mM in EtOH). The surfaces were rinsed with EtOH, then sonicated in EtOH and finally rinsed again in EtOH. The surface was then activated using NHS (0.2M) and EDC (0.8M) in distilled water for 60 min at room temperature. The surface was briefly rinsed with distilled water and blown dry with nitrogen gas. Amino-biotin (Molecular Probes, USA) was added (1 mM in 100 mM carbonate buffer, pH 8.5) and incubated at room temperature for 60 min. After briefly rinsing the surface with distilled water, 50 ug/ml streptavidin (Molecular Probes) in HBST (150 mM NaCl, 0.1% tween 20 and 20 mM Hepes, pH 7.4) and incubated 30 minutes at RT. The surface was washed and 50 ug/ml (diluted in HBST) of the biotinylated biomolecule of choice was applied to the appropriate and incubated for 60 min at RT. An overview is shown in FIG. 1.

Another object of the invention is the combined approach used to immobilize the biomolecules and included special surfaces (gold), hydrophobic thick-film patterning, self-assembling long chain thiols with terminal carboxylic acid groups and an empirically determined EDC/NHS immobilization protocol. While all of these have been used individually, no immobilization protocol exists which combines these various techniques into a single unified protocol.

The immunobilization procedure was empirically optimized by quantitating the amount of radiolabelled streptavidin or human serum albumin. SA and HSA were radiolabelled using the $S^{35}$ protein labeling reagent (SLR) according the manufacturers recommendations (Amersham, UK). For the double labeling HSA was first lightly labeled with biotin, dialyzed and subsequently with SLR. Labeled protein (usually $10^7$ cpm/ug protein) was diluted with unlabeled protein and added to the wells. The amount of material immobilized was quantitated using a Fuji Phosphorimager. The protocol was highly reproducible (n=10, S.D.=5%). Surface density calculations and other evidence indicate that SA is present as a tight monolayer on the surface. AFM as well as ellipsometric experiments indicate the surface is extremely uniform. In addition, we have calculated the SA packing density to be 60,000 SA/mm$^2$ using the radiolabelling data. This is 20% higher than the theoretical packing of 50,000 SA/m$^2$ and can be accounted for by the roughness of the gold surfaces used in these experiments. A gold corn size of 20 nm (determined from atomic force microscopy of the surfaces) corresponds to an accessible area of 70,000 SA/mm$^2$. The a highly reproducible immobilization is absolutely required in order to achieve adequate assay reproducibility and for studying the effects of CRD density gradients.

Figure 2:
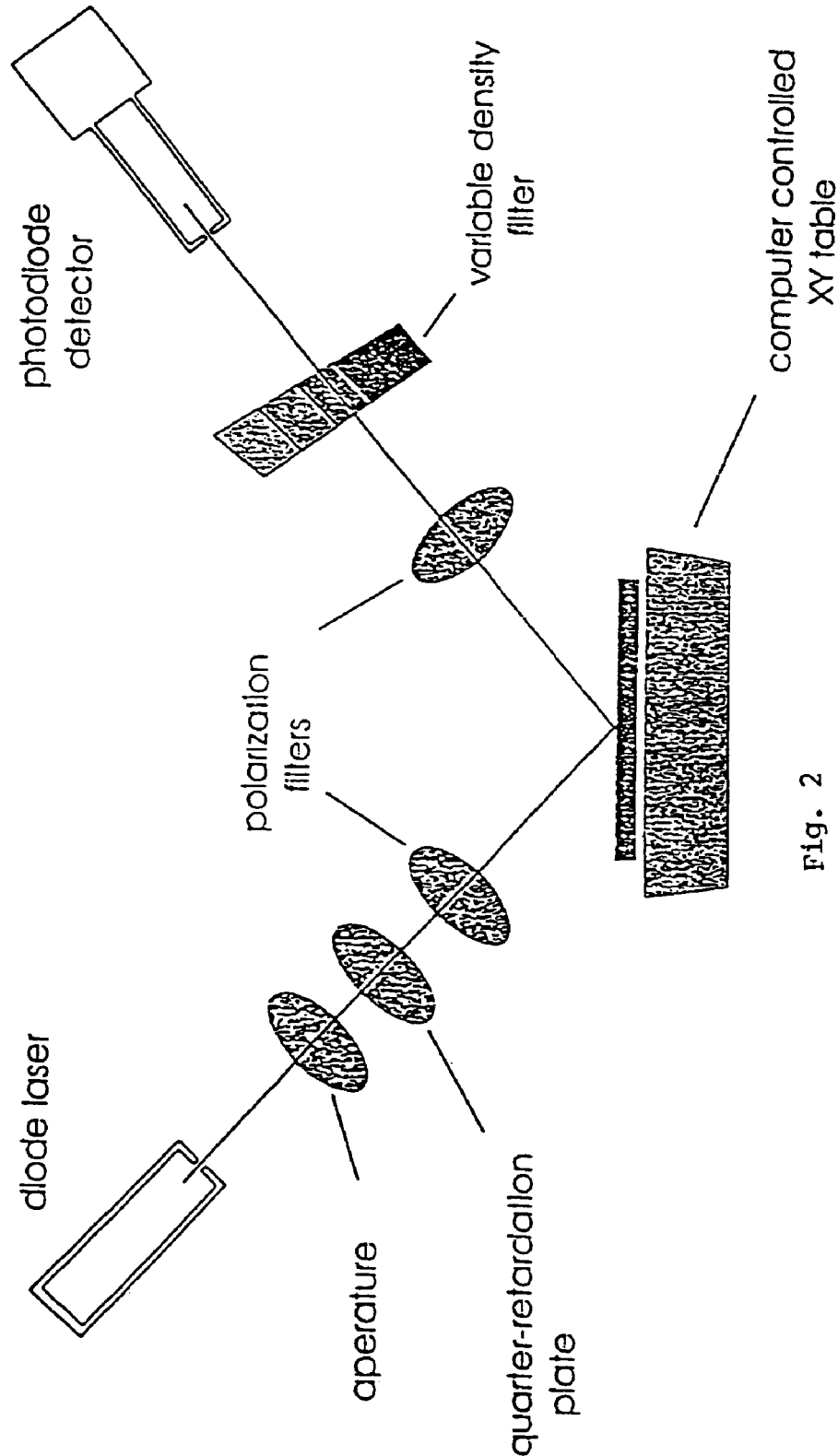
FIG. 2. Schematic of the fixed angle scanning ellipsometer.
Figure 3:
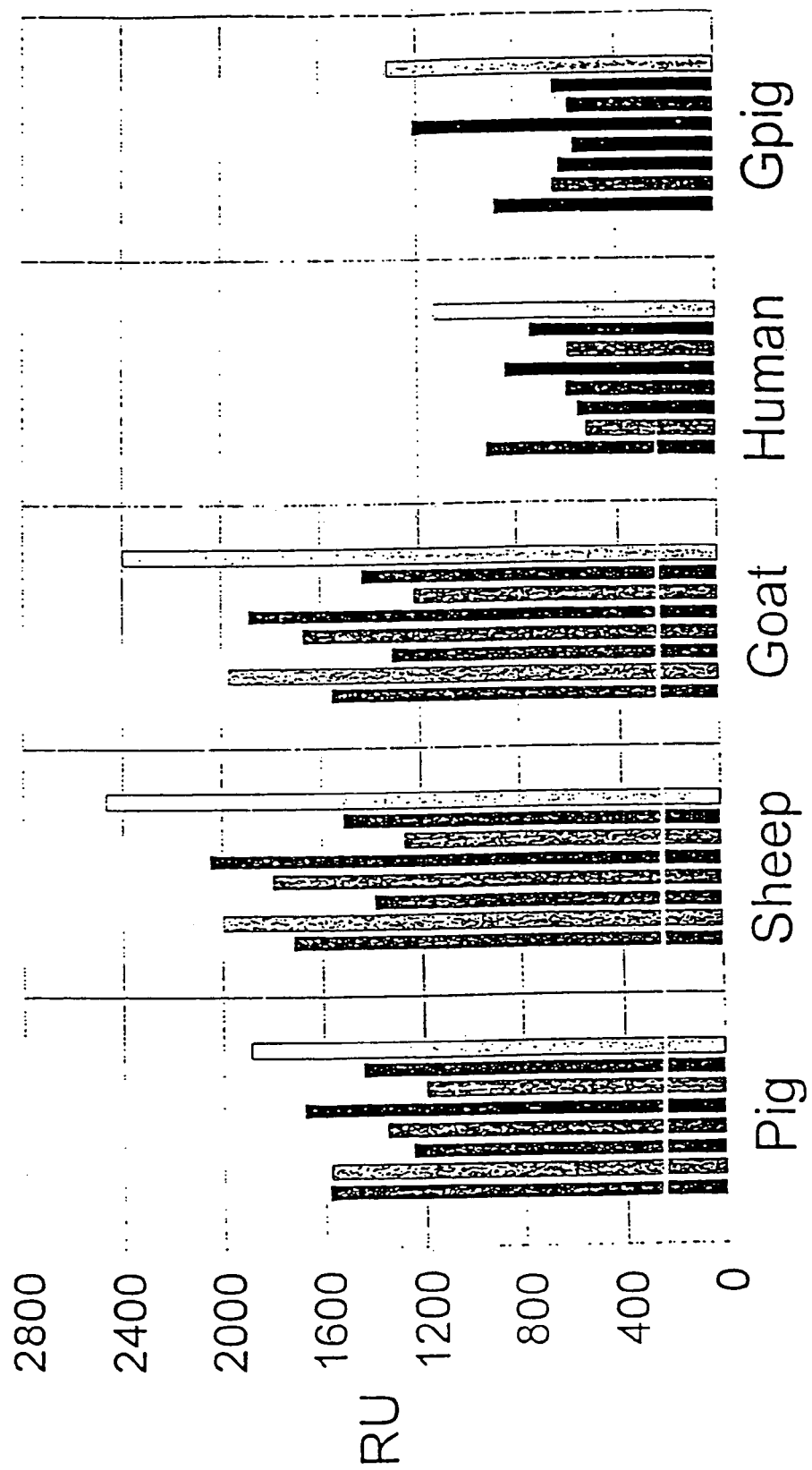
FIG. 3. Chart of the animal sera responses.

This protocol was used to pattern an array of eight biotinylated lectins: *canavalia ensiformis, bandeiraea simplicifolia* BS-I, *arachis hypogaea, phytolacca americana, phaseolus vulgaris* pha-e, *artocarpus integrifolia, triticum vulgaris, pisum sativum*. Pooled sera from Sheep, Goat, Swine and Human (DAKO, Denmark) were diluted 1:4 in HBST and 5 µl was added to each well. After an overnight incubation at 4° C., the samples were washed with buffer and then briefly with distilled water (to remove excess salts which disturbed the ellipsometric measurements). The samples were then placed on the XY stage of a scanning fixed angle ellipsometer which was build at the Laboratory of Applied Physics (Arwin, H., Lundström, I. "Surface oriented optical methods for biomedical analysis," (1988) Method in Enzymology 137:366-381; Jin, G., Tengvall, P., Lundström, I., Arwin, H. A biosensor concept based on imaging ellipsometry for visualization of biomolecular interactions. (1995) Analytical Biochemistry 232:69-72) The apparatus consisted of a 670 nm diode laser (Melles Griot, Sweden) equipped with an aperture, polarisers and a multi-order quarter-retardation plate, arranged in such a way that plane polarized light fell on the sample surface at an appropriate angle. The reflected light was measured using a photodiode. A computer was used to control the position of the sample and to store data obtained from the photodiode. The size of the light spot from the laser was in the order of 1 mm$^2$, thus defining the maximum resolution. The distribution and amount of proteins adsorbed on the surface could then be evaluated or visualized by scanning the sample. The equipment allowed for scan areas up to 20×20 mm with a resolution of up to 200×200 pixels. The experimental arrangement is schematically shown in FIG. 2. The raw values obtained from the experiments were treated with the image analysis program Transform (Spyglass, U.S.A.) or NIH Image to quantitate the data. The data obtained from one such experiment is shown in FIG. 3. This data was input into a three layer artificial neural network consisting of 8 nodes corresponding to the 8 lectins. In the first run, the untreated raw data was input and training quickly lead to convergence, that is to say the net was able to discriminate between the sample.

Example 2

In these studies, sick vs healthy human serum samples were analysed using the same array of eight biotinylated lectins: *canavalia ensiformis, bandeiraea simplicifolia* BS-I, *arachis hypogaea, phytolacca americana, phaseolus vulgaris* pha-e, *artocarpus integrifolia, triticum vulgaris, pisum sativum*. In this case, unpatterned gold (50 nm thick gold evaporated by sputtering) coated glass (0.3 mm thick glass) surfaces were prepared essentially as described above up to and including the coupling of amino-biotin. The surfaces were then inserted into the BIAcore from Pharmacia Biosensor. The running conditions were 2 µl/min, at 25° C. and the running buffer was HBST. The binding of the SA and biotinylated lectins was performed by sequentially injecting 4 µl of a 50 µg/ml solution of each.

Figure 4:
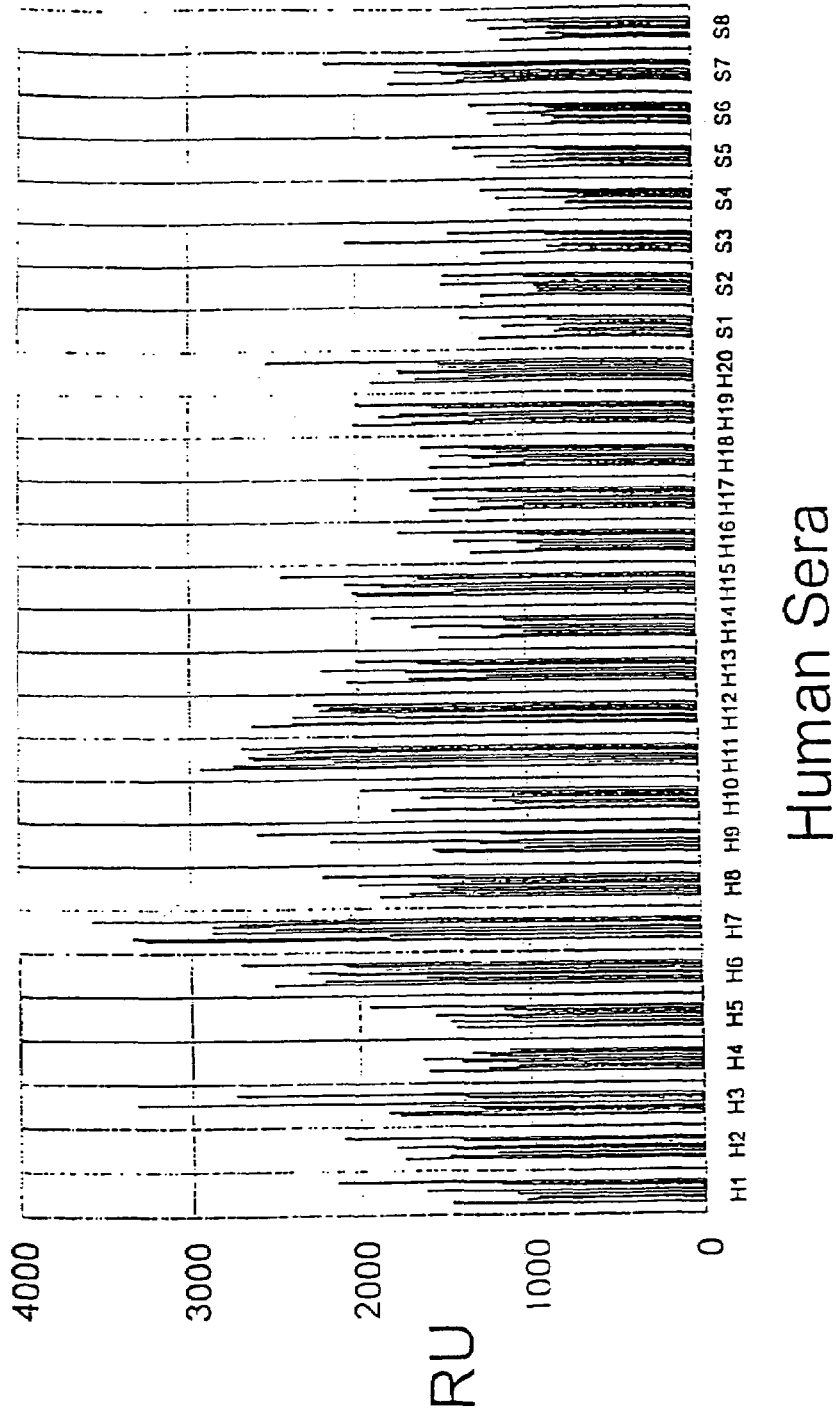
FIG. 4. Chart of the human healthy vs sick responses.

The human sera were obtained from the Infectious Diseases Department at Lunds University Hospital. The reference sera were taken from healthy volunteers (20 individuals). The sick sera samples (8 individuals) all been identified as having clinical bacterial infections. The sera were diluted 4:1 with HBST and 30 µl was injected. After, completion of the injection, a value was taken in reference units (RUs). The surface was regenerated down to the biotin by injecting regeneration solution. SA and biotinylated lectin were then injected sequentially to begin the next binding study. This process was repeated until all of the serum samples had been analysed by all eight lectins. The results from one such experiment are shown in FIG. 4. Seven out of the eight sick individuals can be clearly identified as sick when compared with the healthy reference serum samples.

We originally intended to use antibodies for these studies. However, we were unable to find monoclonal antibodies with an appropriate combination of affinity and specificity. This could be due to the screening procedure used to select these antibodies or possibly due to suppression of broadly cross-reacting antibodies.

The invention claimed is:

1. A method for discriminating complex biological samples, each sample comprising multiple different constituents, the method comprising the steps of:
   (a) providing a sensor array comprising a plurality of sensing fields, each sensing field being at a known location in the array and comprising a plurality of discrete biological sensing elements, the sensing elements being immobilized on the array, each sensing field being characterized by the sensing elements, the plurality of sensing fields being characterized by a plurality of different discrete biological sensing elements;
   (b) contacting a first complex biological sample to the sensor array under conditions that allow binding of some of the constituents of the sample to some of the sensing elements that characterize the sensing fields of the array, wherein constituents bound to the sensing elements in a specific sensing field are bound with a range of affinities and/or specificities;
   (c) removing substantially all of the constituents in the first sample that did not bind to a sensing element;
   (d) analyzing the pattern of binding to construct a first data set by measuring the presence of the sample constituents bound to the sensing elements on each of the sensing fields of the array and expressing said measurement as a numerical value, whereby said values derived from the measurement of each of the sensing fields of the array collectively comprise a data set; and
   (e) comparing the first data set with one or more other data sets, each of the other data sets generated in substantially the same method from other complex biological samples, whereby differences between the data sets can be identified, thus discriminating said samples.

2. The method of claim 1, wherein said measurement of the presence of the sample constituents is performed using a non-label detection system.

3. The method of claim 1 further comprising the step of data analysis of the data set using pattern recognition based data analysis, neural network or statistical based pattern recognition techniques.

4. The method of claim 1, wherein said sensing elements are selected from the group consisting of antibodies, lectins, nucleic acids, carbohydrates, lipids, modified biomolecules and combinations and gradients thereof.

5. The method of claim 1, wherein said sensing element is of nonbiological origin but is endowed with biological-like recognition, said element being selected from the group consisting of cyclodextran and derivatives thereof, roxane and derivatives thereof, templated or imprinted polymers and combinations thereof.

6. The method of claim 4, wherein said sensing elements are lectins selected from the group consisting of canavalia ensiformis, bandciraea simplicifolia BS-1, arachis hypogaea, phytolacca americana, phaseolus vulgaris pha-e, artocarpus integrifolia, triticum vulgaris, pisum sativum.

7. The method of claim 2, wherein said non-label detection system is selected from the group consisting of quartz crystal microbalances, optoacoustics, reflectometry, ellipsometry, SAW and surface plasmon resonance.

8. The method of claim 1, wherein said measuring the presence of the bound sample constituents is performed in imaging mode with a CCD camera.

9. The method of claim 1, wherein said complex biological sample is a bodily fluid obtained from a subject, wherein the subject is an animal or a human.

10. The method of claim 9, wherein the bodily fluid selected from the group consisting of blood, serum, urine, saliva, and sputum.

11. The method of claim 1, wherein said sensing elements are used in gradients in pure and mixed formats and in any combination thereof.

* * * * *

UNITED STATES PATENT AND TRADEMARK OFFICE
CERTIFICATE OF CORRECTION

PATENT NO.         : 7,662,560 B2                          Page 1 of 1
APPLICATION NO. : 11/042984
DATED              : February 16, 2010
INVENTOR(S)        : Mecklenburg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 721 days.

Signed and Sealed this

Thirtieth Day of November, 2010

David J. Kappos
*Director of the United States Patent and Trademark Office*